| United States Patent [19]
Edwards, III

[11] Patent Number: 4,612,391
[45] Date of Patent: Sep. 16, 1986

[54] PREPARATION OF OXYCARBOXYLIC ACIDS

[75] Inventor: William B. Edwards, III, Richmond, Va.

[73] Assignee: Philip Morris Incorporated, New York, N.Y.

[21] Appl. No.: 189,417

[22] Filed: Sep. 22, 1980

[51] Int. Cl.$^4$ ............................................. C07C 59/76
[52] U.S. Cl. .................................. 562/577; 260/413; 562/462; 562/567
[58] Field of Search ............... 562/577, 499, 567, 462; 260/413 Q, 339; 549/431

[56] References Cited

U.S. PATENT DOCUMENTS

| 2,819,279 | 1/1958 | Brown et al. | 260/413 |
| 3,091,620 | 5/1963 | Sturrock et al. | 568/469 |
| 3,219,675 | 11/1965 | Seekircher | 562/577 |
| 3,856,833 | 12/1974 | Siclari et al. | 562/577 |

OTHER PUBLICATIONS

Dauben et al, J. Org. Chem., 23, 1787 (1958).
Dauben et al, J. Org. Chem., 30, 1963 (1965).
Carruthers, W., *Some Modern Methods of Organic Synthesis*, 279, 1971, Cambridge Press.
Chavdarian et al, J. Org. Chemistry, 40, 2970, 1975.

*Primary Examiner*—Werren B. Lone

[57] ABSTRACT

This invention provides a process for the conversion of an alicyclic $\alpha,\beta$-olefinically unsaturated ketone compound to an acyclic oxocarboxylic acid product which contains at least one less carbon atom per molecule than the ketone starting material.

The conversion involves ozonation of the alicyclic $\alpha,\beta$-olefinically unsaturated ketone in an aqueous alcohol reaction medium, followed by a heating step.

20 Claims, No Drawings

PREPARATION OF OXYCARBOXYLIC ACIDS

BACKGROUND OF THE INVENTION

The reaction of ozone with olefinically unsaturated organic compounds has been known for many years, and has been the subject of extensive study. Advances in ozonation chemistry are collected and reported in *Chem. Revs.*, 27, 437 (1940); *Chem. Revs.*, 45, 385 (1949); *Chem. Revs.*, 58, 925 (1958); and "Ozonation in Organic Chemistry", P. S. Bailey, Volume 1, 1978 (Academic Press, N.Y.).

Typically, ozonation reactions are conducted by dissolving the olefin in a solvent and contacting this solution by suitable means with ozone or a mixture of ozone-containing gases at a temperature from about $-100°$ C. to about $30°$ C. The ozonide thus produced is then further treated such as by oxidation to obtain acid products or by reduction if alcohol or aldehyde/ketone products are desired.

Many methods for the preparation of carboxylic acids by the ozonation of unsaturated organic compounds followed by oxidative decomposition of the ozonides are known. Besides oxygen, hydrogen peroxide has been used as oxidant, usually in formic or acetic acids. In these cases the actual oxidizing agent is probably performic or peracetic acid. Silver oxide suspended in sodium hydroxide, potassium permanganate, and chromic acid have also been employed. In order to merge the two reaction steps (ozonation and oxidation) into one, the ozonide or ozone-adduct is reacted immediately after its formation with an oxidizing component which preferably acts also as the reaction medium.

Many methods have been developed for preparing useful products from the ozonides, such as hydrogenation to convert them into alcohols, hydrolysis to convert them into a mixture of aldehydes and acids, oxidation to convert them into acids and the like. In all of the various methods difficulties are usually encountered in controlling the rate of the reaction and the composition of the resulting reaction product.

The ozonolysis of $\alpha,\beta$-unsaturated carbonyl compounds proceeds via an "abnormal" reaction mechanism, i.e., both the olefinic bond and the adjacent single bond connecting the carbonyl group are cleaved, as illustrated by Dauben et al in *J. Org. Chem.*, 23, 1787 (1958):

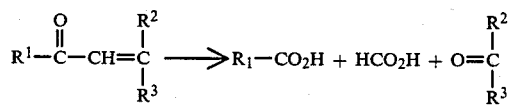

Chavdarian et al in *J. Org. Chem.*, 40, 2970 (1975) report the preparation of a compound such as 5-hydroxy-3,3-dimethylpentanoic acid delta-lactone by ozonation in methanol at $-60°$ C. followed by reduction with sodium borohydride:

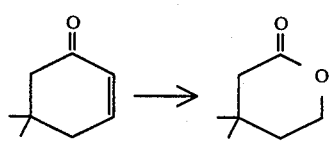

Dauben et al *J. Org. Chem.*, 30, 1693 (1965) report the ozonolysis of 6-isopropyl-3-methyl-2-cyclohexen-1-one to 2-isopropyl-5-oxohexanoic acid. The procedure involves ozonation in methanol followed by reflux with excess 30 percent hydrogen peroxide:

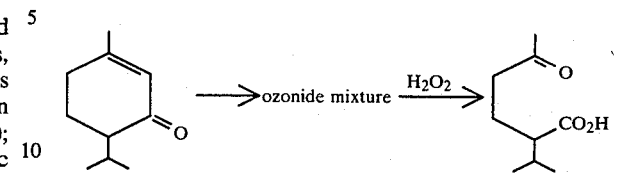

The use of an oxidant such as hydrogen peroxide to convert an ozonide intermediate into carboxylic acid products inherently has several disadvantages. The oxidation reaction is nonselective and tends to attack all oxidizable functionality in the molecules and thereby lowers the yield of desired product. Further, it is necessary to employ a large quantity of a reducing agent such as sodium sulfite to eliminate the excess oxidizing agent at the end of the reaction.

W. Carruthers, "Some Modern Methods of Organic Synthesis", 279, 1971 (Cambridge University Press) also describes the ozonolysis of an $\alpha,\beta$-unsaturated ketone into a keto-acid, wherein the ozonation is performed in acetic acid followed by reflux with excess hydrogen peroxide.

Accordingly, it is an object of this invention to provide an improved process for converting an $\alpha,\beta$-olefinically unsaturated ketone compound to a carboxylic acid product.

It is another object of this invention provide a convenient and efficient method of ozonating an alicyclic $\alpha,\beta$-olefinically unsaturated ketone compound to an oxocarboxylic acid product which contains at least one less carbon atom per molecule than does the ketone starting material.

It is a further object of this invention to provide a process for ozonating an alicyclic $\alpha,\beta$-unsaturated ketone compound to an oxocarboxylic acid product, without the need to treat the ozonide intermediate with a secondary oxidizing agent.

Other objects and advantages of the present invention shall become apparent from the accompanying description and Examples

DESCRIPTION OF THE INVENTION

One or more objects of the present invention are accomplished by the provision of a process for the preparation of an oxocarboxylic acid product which comprises (1) forming a reaction medium by admixing an alicyclic $\alpha,\beta$-olefinically unsaturated ketone compound with a liquid medium comprising an alcohol solvent and between about 5–50 weight percent of water, (2) passing a stream of ozone-containing gas through the reaction medium until substantially all of the ketone compound has interacted with the ozone, wherein the reaction medium is maintained at a temperature between about $-70°$ C. and $50°$ C. during the reaction period; (3) diluting the reaction medium with water, and heating the diluted reaction medium and distilling off substantially all of the alcohol solvent; and (4) recovering from the concentrated aqueous medium an acyclic oxocarboxylic acid product which contains at least one carbon atom less per molecule than the $\alpha,\beta$-olefinically unsaturated ketone starting material.

The invention process is suitable for the ozonolysis of alicyclic $\alpha,\beta$-olefinically unsaturated ketone compounds which have a ring size between about 5–8 carbon atoms, and which do not contain substituents which interfere deleteriously with the ozonolysis reaction mechanisms.

In the following illustrated formulae, R is hydrogen or a $C_1$–$C_4$ alkyl substituent such as methyl, ethyl, propyl, isopropyl, butyl, isobutyl, and the like. R can also be any non-interfering substituent which contains one or more heteroatoms such as nitrogen, sulfur, silicon, phosphorus, halogen, and the like; or two R substituents taken together with connecting atoms can be an alicyclic group (e.g., as represented in cholest-1-en-3-one), or an aromatic group when the two R substituents taken together are not in the $\alpha,\beta$-vinylene positions.

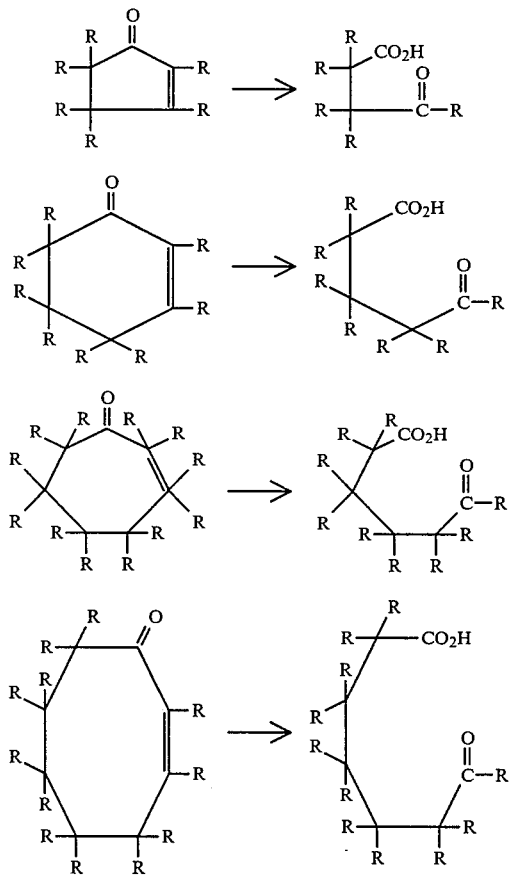

The alcohol solvent employed in the process preferably is a water-miscible monohydric alcohol containing between about 1–8 carbons. Suitable alcohols include methanol, ethanol isopropanol, butanol, isobutanol, pentanol, heptanol, and the like. Preferred alcohols are alkanols containing between about 1–4 carbon atoms. Optionally, an additional solvent component may be included as a non-reactive diluent in the reaction medium, such as dimethylformamide.

The volume of the liquid reaction medium (i.e. the combination of alcohol solvent and water components) normally will be present in a quantity between about 0.4–2 liters per mole of alicyclic $\alpha,\beta$-olefinically unsaturated ketone starting material. It is believed that both the alcohol and water are reactive components, in that they influence or are involved in the ozonolysis reaction mechanisms.

Step (2) of the ozonation procedure is conducted by passing a stream of ozone-containing gas, e.g. 0.5–10 weight percent ozone, through the reaction medium employing a suitable gas dispersion apparatus. The carrier gas component preferably is oxygen or air.

The ozone can be provided by a commercially available ozonator which generally supplies a gas stream containing between about 1–6 weight percent ozone in oxygen or air. For purpose of the ozonation reaction it is preferred to supply the reaction medium with at least the stoichiometric quantity required to produce the ozonide intermediate and convert the intermediate to the final oxocarboxylic acid product. The quantity of supplied ozone should be not less than about 1–2 moles per mole equivalent of $\alpha,\beta$-olefinically unsaturated starting material.

In a typical ozonation procedure, the gas stream is dry oxygen which contains between about 1–5 weight percent of ozone, and the gas stream is passed through the reaction medium at a gas volume rate normally between about 30–300 liters per hour.

The progress of the ozonation reaction can be monitored by sampling the tail gas stream from the reaction zone for its unreacted ozone content. When the tail gas gives a strong test for the presence of ozone the reaction is substantially complete. Alternatively, the disappearance of the starting material can be monitored to determine the ozonation progress.

In the subsequent step (3) of the process, the ozonated reaction medium is diluted with water to provide between about 0.5–5 volumes of water per volume of alcohol in the reaction system.

The diluted reaction is then heated to complete the decomposition of the intermediate ozonide product mixture to the desired oxocarboxylic acid final product. The reaction product medium should be heated to at least above 40° C., and preferably to at least above 60° C., and maintained at the elevated temperature level until the decomposition reaction is completed.

During the said heating period (e.g., at reflux temperature), substantially all of the alcohol solvent and some trace impurities are stripped from the reaction product medium. It is advantageous to sample the reaction product medium during the heating period to ascertain that any oxycarboxylate ester by-product which may have formed has been reconverted to unesterified oxocarboxylic acid as the alcohol component is being removed by distillation.

After the heating and dstilling stages of the process have been completed, the oxocarboxylic acid product is recovered from the concentrated aqueous reaction product medium.

One method of product recovery is preferred when the product mixture is substantially the oxocarboxylic acid without the presence of starting material or by-products which are difficult to separate from the product. In this method of separation, the crude oxocarboxylic acid product is extracted from the concentrated aqueous reaction product medium with a water-immiscible organic solvent. Suitable solvents include dichloromethane, chloroform, carbon tetrachloride, diethyl ether, diisopropyl ether, ethyl acetate, and the like. The oxocarboxylic acid product can be obtained in pure form by fractional distillation of the solvent extract phase or by some other conventional purification method.

Another method of product recovery is preferred when the crude oxocarboxylic acid product is admixed with starting material or by-products which are difficult to separate from the product. In this method of separation, the recovery of oxocarboxylic acid product in step (4) of the invention process is accomplished by (a) adjusting the pH of the concentrated aqueous medium into the alkaline range with a basic reagent, (b) extracting the alkaline aqueous medium with a water-immiscible organic solvent, (c) adjusting the pH of the aqueous medium into the acidic range with an acid reagent, and (d) extracting the oxocarboxylic acid product from the acidic aqueous medium with a water-immiscible organic solvent. The oxocarboxylic acid is recovered in pure form by fractional distillation of the solvent extract phase. Any carboxylic acid by-product present in the extract phase is separated from the desired oxocarboxylic acid product by means of a fractional distillation or other conventional purification method.

In the above-described method of separation, the basic reagent preferably is an alkaline earth or alkali metal carbonate or hydroxide, such as potassium carbonate, sodium hydroxide, calcium hydroxide, and the like.

The water-immiscible organic solvent employed in the two extraction procedures can be of the same type as previously listed above, e.g., dichloromethane.

The acid reagent used for acidifying the aqueous medium preferably is a mineral acid such as hydrochloric acid, sulfuric acid, nitric acid, phosphoric acid, and the like.

The oxocarboxylic acid products produced by the invention process individually find utility as flavorants per se (e.g., for food), as intermediates in the production of flavorants, medicinals or biocides, and other such applications in which the dual functionality of the oxocarboxylic acid compounds is an advantage.

The following examples are further illustrative of the present invention. The specific ingredients and processing parameters are presented as being typical, and various modifications can be derived in view of the foregoing disclosure within the scope of the invention.

EXAMPLE I

Into a stirring solution of 20 grams of 6-isopropyl-3-methyl-2-cyclohexen-1-one in 100 milliliters of methanol/water (80/20) at 0° C. is passed a stream of oxygen containing 2-5 weight percent of ozone until sample analysis indicates that essentially all of the 6-isopropyl-3-methyl-2-cyclohexen-1-one has been reacted. Water (60 milliliters) is added to the solution. The methanol is then removed by atmospheric distillation, after which the concentrated aqueous mixture is heated under reflux until no methyl ester of the product can be detected by gas chmatography.

The mixture is cooled to 5° C., and sodium sulfite is added until a negative starch/iodine test is achieved. The mixture is extracted with methylene chloride. The methylene chloride solution is dried ($Na_2SO_4$), and the methylene chloride is removed under reduced pressure to yield 18.8 grams of an oil. The oil is distilled to give 15.6 grams [bp 103°-4° C. (0.03 mm/Hg)] of 2-isopropyl-5-oxohexanoic acid. Infrared, nuclear magnetic resonance and mass spectra and elemental analysis confirm the structure of the product. Gas chromatography indicates that the product has a purity in excess of 99%.

In a similar manner but with an isopropanol/water (90/10) solvent medium, the following alicyclic $\alpha,\beta$-olefinically unsaturated ketone starting materials yield the indicated oxocarboxylic acid products:

2-Cyclopenten-1-one to 4-oxobutanoic acid
2-Cyclohepten-1-one to 6-oxohexanoic acid
2-Cycloocten-1-one to 7-oxoheptanoic acid

EXAMPLE II

Using the procedure described in Example 1, 20.7 grams of 3,5,5-trimethyl-2-cyclohexen-1-one are converted to 19.5 grams of 3,3-dimethyl-5-oxohexanoic acid [bp 86°-8° C. (0.025/mm/Hg)]. Infrared, nuclear magnetic resonance and mass spectra and elemental analysis confirmed the structure of the product. Gas chromatography indicates a purity in excess of 99%.

EXAMPLE III

Ozonolysis of 18.6 grams of 3,5-dimethyl-2-cyclohexen-1-one is achieved in the manner described in Example I. The aqueous reaction mixture obtained after removal of methanol and addition of sodium sulfite is basified at 5° C. to pH 10 with 50% sodium hydroxide. The aqueous solution is extracted with methylene chloride, acidified at 5° C. to pH 2 with conc. hydrochloric acid and extracted with methylene chloride.

The methylene chloride extracts of the aqueous acid solution are combined and dried ($Na_2SO_4$). The solvent is removed to yield 18.4 grams of an oil. The oil is distilled to give 17 grams of 3-methyl-5-oxohexanoic acid [bp 91°-2° C. (0.03 mm/Hg)]. Infrared, nuclear magnetic resonance and mass spectra and elemental analysis confirm the structure of the product. Gas chromatography indicates a purity in excess of 99%.

EXAMPLE IV

Using the procedure described in Example III, 20.2 grams of 3-methyl-2-cyclohexen-1-one are converted to 16.4 grams of 5-oxohexanoic acid [bp 90°-95° C. (0.01 mm/Hg)]. Infrared, nuclear magnetic resonance and mass spectra and elemental analysis confirm the structure of the product. Gas chromatography indicates a purity in excess of 99%.

EXAMPLE V

Using the procedure described in Example III, 20.2 grams of 3-methyl-2-cyclopenten-1-one are converted to 16.5 grams of 4-oxopentanoic acid [bp 79°-83° C. (0.03 mm/Hg)]. Infrared, nuclear magnetic resonance and mass spectra and elemental analysis confirm the structure of the product. Gas chromatography indicates purity in excess of 99%.

EXAMPLE VI

Using the procedure described in Example III, 19.2 grams of 2-cyclohexen-1-one are converted to 6.4 grams of 5-oxo-pentanoic acid [bp 87°-9° C. (0.03 mm/Hg)]. Gas chromatography indicates the product is contaminated with approximately 2% glutaric acid. Infrared, nuclear magnetic resonance and mass spectra and elemental analysis of a pure sample of the 5-oxopentanoic acid confirm its structure.

EXAMPLE VII

Using the procedure described in Example I except that ethanol/water (80/20) is used as the solvent, 20 grams of 6-isopropyl-3-methyl-2-cyclohexen-1-one are converted to 13.9 grams of 2-isopropyl-5-oxohexanoic acid. It is identical in all respects with the product which is obtained in Example I.

What is claimed is:

1. A process for the preparation of an oxocarboxylic acid product which comprises (1) forming a reaction medium by admixing an alicyclic $\alpha,\beta$-olefinically unsaturated ketone compound having a ring size of between about 5–8 carbon atoms, with a liquid medium comprising an alcohol solvent and between about 5–50 weight percent of water, (2) passing a stream of ozone-containing gas through the reaction medium until substantially all of the ketone compound has interacted with the ozone, wherein the reaction medium is maintained at a temperature between about −70° C. and 50° C. during the reaction period; (3) diluting the reaction medium with water, and heating the diluted reaction medium and distilling off substantially all of the alcohol solvent; and (4) recovering from the concentrated aqueous medium an acyclic oxocarboxylic acid product which contains at least one carbon atom less per molecule than the $\alpha,\beta$-olefinically unsaturated ketone starting material.

2. A process in accordance with claim 1 wherein the alcohol solvent is a water-miscible monohydric alcohol containing between about 1–8 carbon atoms.

3. A process in accordance with claim 1 wherein the alcohol solvent is an alkanol containing between about 1–4 carbon atoms.

4. A process in accordance with claim 1 wherein the gas stream contains between about 0.5–10 weight percent of ozone.

5. A process in accordance with claim 1 wherein the gas stream comprises dry oxygen as the carrier gas component of the gas stream comprises dry oxygen.

6. A process in accordance with claim 1 wherein the gas stream comprises dry air as the carrier gas component of the gas stream comprises dry air.

7. A process in accordance with claim 1 wherein the gas stream is dry oxygen which contains between about 1–5 weight percent of ozone, and the said gas stream is passed through the reaction medium at a gas volume rate between about 30–300 liters per hour.

8. A process in accordance with claim 1 wherein the reaction medium in step (3) is diluted with water to provide between about 0.5–5 volumes of water per volume of alcohol 9. A process in accordance with claim 1 wherein the diluted reaction medium in step (3) is heated to a temperature of at least above 60° C.

10. A process in accordance with claim 1 wherein the recovery of oxocarboxylic acid product in step (4) is accomplished by extracting the said oxocarboxylic acid product from the concentrated aqueous medium with a water-immiscible organic solvent.

11. A process in accordance with claim 1 wherein the recovery of oxocarboxylic acid product in step (4) is accomplished by (a) adjusting the pH of the concentrated aqueous medium into the alkaline range with a basic reagent, (b) extracting the alkaline aqueous medium with a water-immiscible organic solvent, (c) adjusting the pH of the aqueous medium into the acidic range with an acid reagent, and (d) extracting the oxocarboxylic acid product from the acidic aqueous medium with a water-immiscible organic solvent.

12. A process in accordance with claim 1 wherein the $\alpha,\beta$-olefinically unsaturated ketone starting material is 2-cyclopenten-1-one, and the oxocarboxylic acid product is 4-oxobutanoic acid.

13. A process in accordance with claim 1 wherein the $\alpha,\beta$-olefinically unsaturated ketone starting material is 3-methyl-2-cyclopenten-1-one, and the oxocarboxylic acid product is 4-oxopentanoic acid.

14. A process in accordance with claim 1 wherein the $\alpha,\beta$-olefinically unsaturated ketone starting material is 2-cyclohexen-1-one, and the oxocarboxylic acid product is 5-oxopentanoic acid.

15. A process in accordance with claim 1 wherein the $\alpha,\beta$-olefinically unsaturated ketone starting material is 3-methyl-2-cyclohexen-1-one, and the oxocarboxylic acid product 5-oxohexanoic acid.

16. A process in accordance with claim 1 wherein the $\alpha,\beta$-olefinically unsaturated ketone starting material is 6-isopropyl-3-methyl-2-cyclohexen-1-one, and the oxocarboxylic acid product is 2-isopropyl-5-oxohexanoic acid.

17. A process in accordance with claim 1 wherein the $\alpha,\beta$-olefinically unsaturated ketone starting material is 3,5,5-trimethyl-2-cyclohexen-1-one, and the oxocarboxylic acid product is 3,3-dimethyl-5-oxohexanoic acid.

18. A process in accordance with claim 1 wherein the $\alpha,\beta$-olefinically unsaturated ketone starting material is 3,5-dimethyl-2-cyclohexen-1-one and the oxocarboxylic acid product is 3-methyl-5-oxohexanoic acid.

19. A process in accordance with claim 1 wherein the $\alpha,\beta$-olefinically unsaturated ketone starting material is 2-cyclohepten-1-one, and the oxocarboxylic acid product is 6-oxohexanoic acid.

20. A process in accordance with claim 1 wherein the $\alpha,\beta$-olefinically unsaturated ketone starting material is 2-cycloocten-1-one, and the oxocarboxylic acid product is 7-oxoheptanoic acid.

* * * * *